US009555018B2

United States Patent
Consalo et al.

(10) Patent No.: US 9,555,018 B2
(45) Date of Patent: *Jan. 31, 2017

(54) SYNERGISTIC COMBINATIONS OF ORGANIC ACID USEFUL FOR CONTROLLING MICROOGANISMS IN INDUSTRIAL PROCESSES

(71) Applicant: Hercules Incorporated, Wilmington, DE (US)

(72) Inventors: Corinne E. Consalo, New Castle, DE (US); John S. Chapman, Lincoln University, PA (US)

(73) Assignee: Solenis Technologies, L.P., Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/834,259

(22) Filed: Mar. 15, 2013

(65) Prior Publication Data

US 2014/0275264 A1  Sep. 18, 2014

(51) Int. Cl.

| | |
|---|---|
| *A61K 31/194* | (2006.01) |
| *A61K 31/192* | (2006.01) |
| *A61K 31/19* | (2006.01) |
| *A01N 37/02* | (2006.01) |
| *A01N 37/04* | (2006.01) |
| *A01N 37/10* | (2006.01) |
| *A01N 37/36* | (2006.01) |
| *A01N 37/40* | (2006.01) |
| *C12P 7/06* | (2006.01) |
| *C12N 1/14* | (2006.01) |
| *C12N 1/18* | (2006.01) |
| *C12N 1/20* | (2006.01) |

(52) U.S. Cl.
CPC ............ *A61K 31/194* (2013.01); *A01N 37/02* (2013.01); *A01N 37/04* (2013.01); *A01N 37/10* (2013.01); *A01N 37/36* (2013.01); *A01N 37/40* (2013.01); *A61K 31/19* (2013.01); *A61K 31/192* (2013.01); *C12N 1/14* (2013.01); *C12N 1/18* (2013.01); *C12N 1/20* (2013.01); *C12P 7/06* (2013.01); *Y02E 50/17* (2013.01)

(58) Field of Classification Search
None
See application file for complete search history.

(56) References Cited

U.S. PATENT DOCUMENTS

| | | |
|---|---|---|
| 3,600,198 A | 8/1971 | Gunthier et al. |
| 7,642,227 B2 | 1/2010 | Kurtz |
| 7,851,430 B2 | 12/2010 | Kurtz |
| 2003/0203004 A1 | 10/2003 | Kelm et al. |
| 2004/0033289 A1 | 2/2004 | Selmer-Olsen |
| 2006/0204551 A1 | 9/2006 | Manley et al. |
| 2008/0206215 A1 | 8/2008 | Ziegler |
| 2011/0027387 A1 | 2/2011 | Olsen |
| 2011/0054024 A1 | 3/2011 | Maye |
| 2011/0230560 A1 | 9/2011 | Piva et al. |
| 2011/0300257 A1* | 12/2011 | Visser et al. ...................... 426/7 |
| 2012/0003371 A1 | 1/2012 | Ekanayake et al. |
| 2013/0012428 A1 | 1/2013 | Jacobus et al. |

FOREIGN PATENT DOCUMENTS

| | | |
|---|---|---|
| WO | 2007149450 | 12/2007 |
| WO | 2010111639 | 9/2010 |
| WO | 2011038317 | 3/2011 |
| WO | WO 2013/074277 A2 * | 5/2013 |

OTHER PUBLICATIONS

Enegarld-Pulver Zur Herstellung Einer Lösung Zum Eingeben Für Kälber, (Sep. 1, 2009, p. 1, XP055131527 paragraphs [0002], [04.2].

Saithong P et al: "Prevention of bacterial contamination using acetate-tolerant Schizosaccharomyces pombe during bioethanol production from molasses". Journal of Biosciencts and Bioengineering, Elsevier, Amsterdam, NL, vol. 108, No. 3, Sep. 1, 2009, pp. 216-219, XP0264394.

Arto Visti et al: "Preparation of fermentable lingoberry juice through removal of benzoic acid by Saccharomyces cerevisiae yeast". Food Research International vol. 36, No. 6, Jan. 1, 2003, pp. 597-602, XP055073540.

"Scientific Opinion on safety and efficacy of sodium benzoate, proprionic acid and sodium propionate for pigs poultry, bovines, sheep, goats, rabbits, horses, (EFSA Panel on Additives and Products or Substances used in Animal Feed (FEEDAP)", European Food Safety Authority (EFSA), Parma, Italy vol. 2357, Sep. 1, 2011, pp. 1-17, XP055131535.

International Search Report, PCT/US2014/027675, pp. 1-2, Jul. 25, 2014.

* cited by examiner

*Primary Examiner* — San-Ming Hui
*Assistant Examiner* — Andrew Lee
(74) *Attorney, Agent, or Firm* — Joanne Rossi; Michael Herman

(57) ABSTRACT

The present invention provides a method of controlling bacterial contamination using synergistic interactions of antimicrobials. The invention utilizes a combination of organic acids where the combined antimicrobial effect is synergistic.

20 Claims, No Drawings

SYNERGISTIC COMBINATIONS OF ORGANIC ACID USEFUL FOR CONTROLLING MICROOGANISMS IN INDUSTRIAL PROCESSES

FIELD OF THE INVENTION

The invention relates to synergistic combinations of antimicrobials and methods of their use for the control of microorganisms in industrial processes, materials, or products.

BACKGROUND OF THE INVENTION

Microorganisms, such as yeast, fungi and bacteria, are used to produce a number of fermentation products, such as industrial grade ethanol, distilled spirits, beer, wine, pharmaceuticals and nutraceuticals (foodstuff that provides health benefits, such as fortified foods and dietary supplements), baking industry and industrial chemicals.

Yeast is commonly used in fermentation processes. One common type of yeast is *Saccharomyces cerevisiae*, the species predominantly used in baking and fermentation. Non-*Saccharomyces* yeasts, also known as non-conventional yeasts, are also used to make a number of commercial products.

Other microorganisms can also be useful in making fermentation products. For example, cellulosic ethanol production, production of ethanol from cellulosic biomass, utilizes fungi and bacteria. Examples of these cellulolytic fungi include *Trichoderma reesei* and *Trichoderma viride*. One example of a bacteria used in cellulosic ethanol production is *Clostridium ljungdahlii*.

Most of the yeast used in distilleries and fuel ethanol plants are purchased from manufacturers of specialty yeasts. The yeast is manufactured through a propagation process. Propagation involves growing a large quantity of yeast from a small lab culture of yeast. During propagation, the yeast are provided with the oxygen, nitrogen, sugars, proteins, lipids and ions that are necessary or desirable for optimal growth through aerobic respiration.

Once at the distillery, the yeast can undergo conditioning. Conditioning is unlike propagation in that it does not involve growing a large quantity from a small lab culture. During conditioning, conditions are provided to re-hydrate the yeast, bring them out of hibernation and allow for maximum anaerobic growth and reproduction. The objective of both propagation and conditioning is to deliver a large volume of yeast to the fermentation tank with high viability, high budding and a low level of infection by other microorganisms.

Following propagation and/or conditioning, the yeast enters the fermentation process. The yeast is combined in an aqueous solution with fermentable sugars. The yeast consumes the sugars, converting them into aliphatic alcohols, such as ethanol.

The fermentation process begins with the preparation of a fermentable carbohydrate. In ethanol production, corn is one possible fermentable carbohydrate. Other carbohydrates including cereal grains and cellulose-starch bearing materials, such as wheat or milo, could also be substituted. Cellulosic biomass such as straw and cornstalks could also be used. Cellulosic ethanol production has recently received attention because it uses readily available nonfood biomass to form a valuable fuel.

The propagation, conditioning and fermentation processes can be carried out using batch or continuous methods. The batch process is used for small-scale production. Each batch is completed before a new one begins. The continuous fermentation method is used for large-scale production because it produces a continuous supply without restarting every time.

During the propagation, conditioning or fermentation process the mash or the fermentation mixture can become contaminated with other microorganisms, such as spoilage bacteria. These microorganisms compete with the desired species of yeast for fermentable sugars and other fermentable carbohydrates and retard the desired bio-chemical reaction resulting in a lower product yield. They can also produce unwanted chemical by-products, which can cause spoilage of entire fermentation batches.

Producers of ethanol attempt to increase the amount of ethanol produced from one bushel of cereal grains (approximately 56 pounds (25.4 kilograms)). Contamination by microorganisms lowers the efficiency of yeast making it difficult to attain or exceed the desired levels of 2.8-2.9 gallons of ethanol per bushel (0.42-0.44 liters per kilogram). Reducing the concentration of microorganisms will encourage yeast propagation and/or conditioning and increase yeast efficiency making it possible to attain and exceed these desired levels.

During any of these three processes the yeast can become contaminated with undesirable yeast, bacteria or other undesirable microorganisms. This can occur in one of the many vessels used in propagation, conditioning or fermentation. This includes, but is not limited to, propagation tanks, conditioning tanks, starter tanks, fermentations tanks and piping and heat exchangers between these units.

Bacterial or microbial contamination reduces the fermentation product yield in three main ways. First, the sugars that could be available for yeast to produce alcohol are consumed by the bacteria or other undesirable microorganisms and diverted from alcohol production, reducing yield. Second, the end products of bacterial metabolism, such as lactic acid and acetic acid, inhibit yeast growth and yeast fermentation/respiration, which results in less efficient yeast production. Finally, the bacteria or other undesirable microorganisms compete with the yeast for nutrients other than sugar.

After the fermentation system or vessel has become contaminated with bacteria or other undesirable microorganisms, those bacteria or other microorganisms can grow much more rapidly than the desired yeast. The bacteria or other microorganisms compete with the yeast for fermentable sugars and retard the desired bio-chemical reaction resulting in a lower product yield. Bacteria also produce unwanted chemical by-products, which can cause spoilage of entire fermentation batches. Removing these bacteria or other undesirable microorganisms allows the desired yeast to thrive, which results in higher efficiency of production.

As little as a one percent decrease in ethanol yield is highly significant to the fuel ethanol industry. In larger facilities, such a decrease in efficiency will reduce income from 1 million to 3 million dollars per year.

Some methods of reducing bacteria or other undesirable microorganisms during propagation, conditioning and fermentation take advantage of the higher temperature and pH tolerance of yeast over other microorganisms. This is done by applying heat to or lowering the pH of the yeast solution. However, these processes are not entirely effective in retarding bacterial growth. Furthermore, the desirable yeast microorganisms, while surviving, are stressed and not as vigorous or healthy. Thus, the yeasts do not perform as well.

The predominant trend in the ethanol industry is to reduce the pH of the mash (feed stock) to less than 4.5 at the start of fermentation. Lowering the pH of the mash reduces the population of some species of bacteria. However it is much less effective in reducing problematic bacteria, such as lactic-acid producing bacteria. It also significantly reduces ethanol yield by stressing the yeast used for ethanol production.

Another approach involves washing the yeast with phosphoric acid. This method does not effectively kill bacteria and other microorganisms. It can also stress the yeast used for ethanol production, thereby lowering their efficiency.

Yet another method is to use heat or harsh chemicals to sterilize process equipment between batches. It is ineffective at killing bacteria and other microorganisms within the yeast mixture during production.

In yet another method, antibiotics are added to yeast propagation, conditioning or fermentation batch to neutralize bacteria. Fermentation industries typically apply antibiotics to conditioning, propagation and fermentation processes. Antibiotic dosage rates range between 0.1 to 3.0 mg/L and generally do not exceed 6 mg/L. However, problems exist with using antibiotics in conditioning, propagation and fermentation. Antibiotics are expensive and can add greatly to the costs of large-scale production. Moreover, antibiotics are not effective against all strains of bacteria, such as antibiotic-resistant strains of bacteria. Overuse of antibiotics can lead to the creation of additional variants of antibiotic-resistant strains of bacteria.

Antibiotic residues and establishment of antibiotic-resistant strains is a global issue. These concerns may lead to future regulatory action against the use of antibiotics. One area of concern is distillers grain that are used for animal feed. Distillers grain is the grain residue of the fermentation process. European countries do not allow the byproducts of an ethanol plant to be sold as animal feed if antibiotics are used in the facility. Distiller grain sales account for up to 20% of an ethanol plant earnings. Antibiotic concentration in the byproduct can range from 1-3% by weight, thus negating this important source of income.

In addition, there are other issues to consider when using antibiotics. Mixtures of antibiotics should be frequently balanced and changed in order to avoid single uses that will lead to antibiotic-resistant strains. Sometimes the effective amount of antibiotic cannot be added to the fermentation mixture. For example, utilizing over 2 mg/L of Virginiamycin will suppress fermentation but over 25 mg/L is required to inhibit grown of *Weisella confusa*, an emerging problematic bacteria strain. Overdosing or overuse of antibiotic can stress yeast and impact efficiency or cause regulatory non-compliance.

Industries that employ fermentation for beverages have historically applied hops acid to propagation and fermentation to control unwanted microbes that compete with the yeast for nutrients. With the recent expansion of fuel ethanol, hops acids have been utilized to a minor degree to address unwanted, gram positive microbes. Competition between yeasts and unwanted microbes results yield loss of fuel ethanol as unwanted microbes, primarily *Lactobacillus* and *Acetobacter*, reduce the efficiency of fermentation. In beverage, competing microbes not only reduce efficiency but can alter the aesthetics and taste of the final product.

Organic acid have many applications, including being used as acidifiers, buffers, antioxidants, chelators, synergists, dietary supplements, flavoring agents, preservatives and antimicrobials. Organic acids have been used as preservatives because of their effect on bacteria. The mode of action of organic acid is that the non-dissociated acids penetrate the bacterial cell wall via passive diffusion and disrupt the normal physiology of the cell in two ways: The acids dissociate and therefore lower the internal pH, which is normally close to neutral, impairing the function of the bacteria. The anionic part of the acid that is unable to leave the cell in its dissociated form accumulates within, disrupting metabolic functions and increasing osmotic pressure.

Since small decreases in ethanol yield are highly significant to the fuel ethanol industry, ethanol producers are constantly looking for ways to increase efficiency. Antimicrobials are used to eliminate, reduce or otherwise control the number of microbes in the aqueous systems. However, the use of antimicrobials will always add cost to operations and products. In addition, some antimicrobials may have deficiencies in either their spectrum of antimicrobial action or operational limitations in their manner of application, such as lack of temperature stability or susceptibility to inactivation by environmental or chemical factors.

It is known that the presence of microorganisms in industrial water systems is a significant problem in industrial processes, causing issues with decreased product yields and product quality. One specific example of this is in corn-to-ethanol biorefining, where lactic acid bacteria are introduced into the process via corn stocks. During fermentation, these bacteria compete with ethanol producing yeast for substrate and nutrients, which lowers ethanol yield. Currently, almost all U.S. biorefining plants utilize an antimicrobial agent and many of them use antibiotics such as virginiamycin. An important product of corn biorefining is dried distillers grains for use as animal feed, and the market for antibiotic-free feed grains is growing. It is expected that the FDA will soon form regulations reducing or eliminating antibiotic use in animal feed. Canada has similar concerns regarding antibiotics in distillers grains and most of their production is exported. Europe has already banned the use of antibiotics in ethanol plants where distillers grains are produced for animal feed. In Brazil, operating antibiotic-free is mandatory in plants producing yeast extract for export.

The control of microbes is very significant to many industries and the predominant strategy is treatment with antimicrobials. Antimicrobials are used to eliminate, reduce or otherwise control the number of microbes in aqueous systems. However, the use of most antimicrobials will add cost to operations and products and thus more effective ways to achieve microbial control are sought. In addition, many antimicrobials have deficiencies in either their spectrum of antimicrobial action or operational limitations in their manner of application such as lack of temperature stability or susceptibility to inactivation by environmental or chemical factors.

Therefore, combinations of antimicrobials may be used, and in particular, synergistic combinations of antimicrobials are preferred. Synergistic combinations of antimicrobials can deliver an antimicrobial effect greater than the sum of the individual antimicrobials and thus can provide an improved cost performance over those combinations which are merely additive in terms of antimicrobial efficacy.

DESCRIPTION OF THE INVENTION

For the purposes of this specification, the meaning of "microorganisms" and "microbes" includes, but is not limited to, bacteria, fungi, algae, protozoans, and viruses. Preferred microbes against which the compositions of the invention are effective are bacteria. Examples of undesirable bacteria include, but are not limited to, lactic acid producing bacteria, acetic acid producing bacteria, and other bacteria which contaminate ethanol fermentation processes. It is also understood that the microbes within aqueous systems can be located suspended within the fluid (eg, planktonic) or localized on a surface in contact with the aqueous system (eg, biofilms). The words and phrases "control", "microbial control", "controlling", and "antimicrobial efficacy" should be construed to include within their meaning, without being limited to, inhibiting the growth of microbes, killing microbes, disinfection, preservation, sanitization, or preventing the re-growth of microbes.

As used herein ppm is measured as mass per volume or 1 ppm equals 1 mg (active) per liter.

As used herein the term "organic acid" is also referring to its salt.

The present invention provides synergistic antimicrobial aqueous compositions comprising combinations of at least one first organic acid and at least one second organic acid and method of using the combinations of at least one first organic acid and at least one second organic acid. The organic acids can be used in their acid form or their salt form. These combinations are useful for controlling microorganisms in aqueous systems and products. The present invention results in a significant reduction of the number of contaminating bacteria in industrial processes, materials, or products where their presence is considered undesirable.

It has been discovered that using the combinations of at least two organic acids or their salts, provides synergistic microbial control in aqueous systems. Thus, the combination of components result in improved antimicrobial efficacy beyond that which would be expected based on the sum of their individual antimicrobial efficacies. This unexpectedly observed synergy permits reduced amounts of the antimicrobials to be used to achieve acceptable microbial control in industrial processes such as biorefining or materials where desired.

A first organic acid or component and a second organic acid or component which is not the same acid as the first acid or component is useful in the present invention. Suitable, non-limiting examples of organic acids useful in the present invention include but are not limited to citric acid, benzoic acid, propionic acid, tartaric acid, acetic acid, benzenesulfonic acid, oxalic acid, malic acid, salicylic acid, lactic acid gluconic acid, hydroxyacetic acid and their salts. For purposes of this invention the organic acid is not a hops acid. Preferred first acids or components include citric acid, propionic acid, and benzoic acid or their salts. Preferred second acids or components include propionic acid, benzoic acid, or their salts with the provisio that the first acid and the second acid are different acids. For purposes of example only, if citric acid or its salt is the first component then citric acid or its salt cannot be the second component. The organic acids can be in their acid form or their salt form when used in the present invention.

One embodiment of the invention is citric acid as the first acid in combination with at least one second organic acid, in particular the second acid can be propionic acid or benzoic acid or their salts.

Examples of aqueous systems in which the compositions are useful are biorefining processes, industrial fermentations, cooling water, boiler water, pulp and paper mill water, oil and gas field injection water and produced water, oil and gas pipelines and storage systems, fuel, ballast water, wastewater, pasteurizers, other industrial process water, metalworking fluids, latex, polymers, paint, coatings, adhesives, inks, personal care and household products, reverse osmosis systems, electrochemical deposition systems, fluids used in mineral extraction, mineral slurries, agricultural processing, biorefining waters, and systems that use them. In addition, the compositions may be used in other areas where microbial contamination of aqueous systems occurs.

Unwanted or undesirable microbes in an industrial process are those which by virtue of their physical presence or metabolic activity impair the efficiency or yield of that process. Thus for example microbes growing on the surface of a heat exchanger impair its efficiency at transferring heat (due to the insulating properties of their bodies and assorted exopolymers), while microbes utilizing the components of a process as a food source (e.g. cellulose in a pulping operation) or altering the pH of a process by excreting organic acid (metabolic by product) are undesirable. Non-limiting examples of undesirable bacteria include the lactic acid producing bacteria (LAB) and the acetic acid producing bacteria of which *Lactobacillus* and *Acetobacter* are prominent representatives.

These combinations of organic acids can be used in the biorefining industry and fermentation systems.

The pH of the aqueous system to be treated is generally is from 3 to 11, or from 3 to 7, or from 4 to 9, or from 4 to 8, or from 4 to 6.5, or from 4.5 to 6. In general, the organic acids work best in systems where the pH of the system is less than at least one of the pKa values of the acid or its salt.

The components of the composition can be added to the aqueous system to be treated sequentially or combined and then added to the system to be treated. The organic acids can be added to the aqueous side systems with other additives such as, but not necessarily restricted to, surfactants, scale and corrosion control compounds, ionic or non-ionic polymers, pH control agents, and other additives used for altering or modifying the chemistry of the aqueous system. The organic acids are added to the systems to be treated in the ratios of the first acid to the second acid of from 64:1 up to 1:32, or ratios of from 32:1 to 1:32, or ratios of from 32:1 to 1:16, or ratios of from 8:1 to 1:32, or ratios of from 8:1 to 1:16 or ratios of from 8:1 to 1:8.

A person of ordinary skill in the art can readily determine the concentration of the composition required to achieve acceptable microbial control, and that the concentration is dependent on the matrix. The first acid can be used in amounts of from 12500 ppm down to 100 ppm in the system to be treated. The first acid could be used in amount of from 6250 down to 100 ppm in the aqueous system to be treated or from 4000 down to 100 ppm or from 4000 down to 200 ppm. Generally at least 100 ppm or at least 200 ppm or at least 300 ppm of the first acid is used. The ratio of the first acid to second organic acid can be from than 64:1 to 1:32 or from 32:1 to 1:32 or from 8:1 to 1:32. Generally the sum total amount of the two organic acid used in the system being treated is less than 20,000 ppm, or less than 15,000 ppm or less than 11,000 ppm. Generally the sum total amount of the two acids used in the system being treated is at least 200 ppm or at least 400 ppm.

In one embodiment the organic acid is citric and the ratio of citric acid to second organic acid can be from 32:1 to 1:32 or from 8:1 to 1:32 or from 8:1 to 1:16. The second acid is selected from propionic acid, benzoic acid or their salts. Citric acid can be used in amounts of from 12500 ppm down to 100 ppm in the aqueous system to be treated. Citric acid could be used in amount of from 6250 down to 200 ppm or from 4000 down to 200 ppm or from 4000 down to 300 ppm in the aqueous system to be treated. Generally at least 100 ppm, or at least 200 ppm, or at least 300 ppm of citric acid or its salt is used in the aqueous system to be treated.

In one embodiment of the invention the at least one first organic acid comprises citric acid, the at least one second organic acid comprises propionic acid or its salt, in which the ratio of citric acid to propionic acid is from 64:1 to 1:16 and the amount of the first organic acid is the aqueous system to be treated is from 200 to 1000 ppm.

In one embodiment of the invention the at least one first organic acid comprises citric acid, the at least one second organic acid comprises benzoic acid or its salt, wherein the ratio of citric acid to benzoic acid is from 8:1 to 1:32, and the amount of the first organic acid is the aqueous system to be treated is from 200 to 1000 ppm.

Examples of undesirable bacteria for which the invention is useful include lactic-acid producing bacteria or acetic acid producing bacteria. These include, but are not limited to, *Lactobacillus* and *Acetobacter*.

When used in a fermentation system the acids can be added in various locations in the fermentation system such as can be added in single or multiple locations in the fermentation process, including the slurry tank(s), cookers, mash coolers, propagators and fermentation tanks. One skilled in the art may also determine other addition points.

In fermentation systems using the present method, the concentrations of bacteria and other undesirable microorganisms can be reduced while propagation and/or conditioning of desirable microorganisms is encouraged. It has been discovered that a first organic acid in combination with at least one second organic acid is effective at reducing the concentration of undesirable bacteria and other undesirable microorganisms while simultaneously encouraging propagation and/or conditioning of desirable microorganisms. The combination of these products provides a synergistic, antimicrobial treatment without the use of antibiotics.

One non-limiting embodiment of the current method for reducing undesirable microorganism concentration, promoting desirable microorganism propagation, and increasing desirable microorganism efficiency in an aqueous system comprises:
  (a) introducing a fermentable carbohydrate to an aqueous system,
  (b) introducing at least one yeast or desirable microorganism to the aqueous system, and
  (c) contacting a first organic acid and a second organic acid with the fermentable carbohydrate and or yeast.

These steps can be performed sequentially or in a different order. The first organic acid and second organic acid can be brought into contact with the yeast or with the fermentation carbohydrate or the yeast and the fermentable carbohydrate can be combined and then the first organic acid and second organic acid be introduced into the combination of yeast and carbohydrate. The first organic acid and second organic acid can be blended together and then added to the aqueous system or they can be added separately to the aqueous system. The aqueous system can be in a continuous process or may be a tank in the case of a batch process.

Another non-limiting embodiment of the current method for reducing undesirable microorganism concentration, promoting yeast propagation, and increasing yeast efficiency in an aqueous system comprises
  (a) introducing a quantity of fermentable carbohydrate to an aqueous system,
  (b) introducing a quantity of yeast to the aqueous system, and
  (c) contacting first organic acid and second organic acid with the fermentable carbohydrate and or yeast These steps can be performed sequentially or in a different order. The first organic acid and second organic acid can be blended together and then added to the aqueous system or they can be added separately to the aqueous system.

In the foregoing method, the "undesirable" microorganisms intended to be reduced are those that compete for nutrients with the desirable microorganisms that promote the desired fermentation processes. In this regard, first organic acid and second organic acid employed in the present method do not detrimentally affect the growth and viability of desirable, fermentation-promoting microorganisms, but does eliminate or suppress the growth of undesirable microorganisms that interfere with the fermentation process. Moreover, the elimination or suppression of undesirable microorganisms has a favorable effect on the growth and viability of desirable microorganisms.

The production of fuel ethanol by yeast fermentation is used as an example of where the present invention can be used. Other fermentation products which could employ the combination of the first organic acid in conjunction with the second organic acid could include distilled spirits, beer, wine, pharmaceuticals, pharmaceutical intermediates, baking products, nutraceuticals (foodstuff that provides health benefits, such as fortified foods and dietary supplements), nutraceutical intermediates, industrial chemical feedstocks, and enzymes. The current method could also be utilized to treat yeast used in the baking industry.

Yeast is not the only microorganism used in fermentation. Additional desirable fermenting microorganisms could also be used and benefited by the invention such as the fungi and bacteria typically used in cellulosic ethanol production. Some non-limiting examples of desirable fermenting microorganisms include, but are not limited to, *Trichoderma reesei*, *Trichoderma viride*, and *Clostridium ljungdahlii*.

The first organic acid in conjunction with the second organic acid can be added at various points in the propagation, conditioning and/or fermentation processes. The first organic acid in conjunction with the second organic acid can be added to cook vessels, fermentation tanks, propagation tanks, conditioning tanks, starter tanks or during liquefaction. The first organic acid in conjunction with the second organic acid can also be added directly to the corn mash. The first organic acid in conjunction with the second organic acid can also be added to the interstage heat exchange system or heat exchangers. The first organic acid in conjunction with the second organic acid can also be added to the piping between these units or heat exchangers.

The first organic acid in conjunction with the second organic acid can be added directly into the fermentation mixture. This can be done by adding the first organic acid and second organic acid in conjunction with the yeast or other desirable microorganism and fermentable carbohydrate, for example during the SSF (Simultaneous saccharification and fermentation) stage. The first organic acid dosages of between 200 and 10000 ppm or 200 and 5000 ppm and the second organic acid dosages of between 200 and 10000 ppm or 200 and 5000 ppm can be added directly into the fermentation mixture.

The first organic acid in conjunction with the second organic acid can also be added to the mash prior to the fermentation process. The first organic acid dosages of between 200 and 10000 ppm or 200 and 5000 ppm and organic acid dosages of between 200 and 10000 ppm or 200 and 5000 ppm can be added to the mash prior to fermentation.

The first organic acid in conjunction with the second organic acid can also be added during propagation and/or conditioning. For example the first organic acid and the second organic acid can be added to the yeast slurry replacing an acid washing step.

The first organic acid in conjunction with the second organic acid can be used to achieve improved results in the production of cellulosic ethanol. Cellulosic ethanol is a type of ethanol that is produced from cellulose, as opposed to the sugars and starches used in producing carbohydrate based ethanol. Cellulose is present in non-traditional biomass sources such as switch grass, corn stover and forestry. This type of ethanol production is particularly attractive because of the large availability of cellulose sources. Cellulosic ethanol, by the very nature of the raw material, introduces higher levels of contaminants and competing microorganism into the fermentation process. The first organic acid used in conjunction with the second organic acid can be used in cellulosic ethanol production to control undesirable microorganisms.

There are two primary processes of producing alcohol from cellulose. One process is a hydrolysis process that utilizes fungi, as for example *Trichoderma reesei* and/or *Trichoderma viride*. The other is a gasification process using a bacteria such as *Clostridium ljungdahlii*. The first organic acid in conjunction with the second organic acid can be utilized in either process.

In the hydrolysis process the cellulose chains are broken down into five carbon and six carbon sugars before the fermentation process. This is either done chemically and enzymatically.

In the chemical hydrolysis method the cellulose can be treated with dilute acid at high temperature and pressure or concentrated acid at lower temperature and atmospheric pressure. In the chemical hydrolysis process the cellulose reacts with the acid and water to form individual sugar molecules. These sugar molecules are then neutralized and yeast fermentation is used to produce ethanol. The first organic acid in conjunction with the second organic acid can be used during the yeast fermentation portion of this method.

Enzymatic hydrolysis can be carried out using two methods. The first is known as direct microbial conversion (DMC). This method uses a single microorganism to convert the cellulosic biomass to ethanol. The ethanol and required enzymes are produced by the same microorganism. The first organic acid in conjunction with the second organic acids can be used during the propagation/conditioning or fermentation steps with this specialized organism.

The second method is known as the enzymatic hydrolysis method. In this method cellulose chains are broken down using cellulase enzymes. These enzymes are typically present in the stomachs of ruminants, such as cows and sheep, to break down the cellulose that they eat. In this process the cellulose is made via fermentation by cellulolytic fungi such as *Trichoderma reesei* and *Trichoderma viride*. The enzymatic method is typically carried out in four or five stages. The cellulose is pretreated to make the raw material, such as wood or straw, more amenable to hydrolysis. Next the cellulase enzymes are used to break the cellulose molecules into fermentable sugars. Following hydrolysis, the sugars are separated from residual materials and added to the yeast. The hydrolyzate sugars are fermented to ethanol using yeast. Finally, the ethanol is recovered by distillation. Alternatively, the hydrolysis and fermentation can be carried out together by using special bacteria or fungi that accomplish both processes. When both steps are carried out together the process is called sequential hydrolysis and fermentation (SHF).

The first organic acid and second organic acid can be introduced for microbiological efficacy at various points in the enzymatic method of hydrolysis. The first organic acid in conjunction with second organic acid can be used in the production, manufacture and fermentation of cellulase enzymes made by *Trichoderma* and other fungi strains. The first organic acid and second organic acid can be added in the cellulosic simultaneous saccharification and fermentation phase (SSF). The first organic acid and second organic acid can be introduced in the sequential hydrolysis and fermentation (SHF) phase. They could also be introduced at a point before, during or after the fermentation by cellulolytic fungi that create the cellulase enzymes. Alternatively the first organic acid and second organic acid can be added during the yeast fermentation phase, as discussed above.

The gasification process does not break the cellulose chain into sugar molecules. First, the carbon in the cellulose is converted to carbon monoxide, carbon dioxide and hydrogen in a partial combustion reaction. Then, the carbon monoxide, carbon dioxide and hydrogen are fed into a special fermenter that uses a microorganism such as *Clostridium ljungdahlii* that is capable of consuming the carbon monoxide, carbon dioxide and hydrogen to produce ethanol and water. Finally, the ethanol is separated from the water in a distillation step. The first organic acid in conjunction with second organic acid can be used as an antimicrobial agent in the fermentation step involving microorganisms such as *Clostridium ljungdahlii* that are capable of consuming carbon monoxide, carbon dioxide and hydrogen to produce ethanol and water.

In one non-limiting embodiment, first organic acid and second organic acid are added to a tank and diluted to a predetermined concentration at a predetermined ratio. In the tank, the first organic acid and second organic acid are dissolved in water to form a first organic acid and second organic acid blend. The concentration of the first organic acid and second organic acid in the batch tank can vary across a wide range. The first organic acid and second organic acid is then exhausted from the batch tank through an outlet at a specified dosage rate to create a solution of the desired concentration.

EXAMPLES

The synergy indices reported in the following examples use the following formula, which was first reported in F. C. Kull, P. C. Eisman, H. D. Sylwestrowka, and R. L. Mayer, Letts. In Applied Microbiology 9:538-541, 1961:

Synergy Index=$Qa/QA+Qb/QB$ where Qa is the concentration of Antimicrobial A required to achieve complete inhibition of growth of the test microbe when used in combination with Antimicrobial B;
QA is the concentration of Antimicrobial A required to achieve complete inhibition of growth of the test microbe when used alone;
Qb is the concentration of Antimicrobial B required to achieve complete inhibition of growth of the test microbe when used in combination with Antimicrobial A;
QB is the concentration of Antimicrobial B required to achieve complete inhibition of growth of the test microbe when used alone.

A synergy index (SI) of 1 indicates the interactions between the two antimicrobials is merely additive, a SI of greater than one indicates the two antimicrobials are antagonistic with each other, and a SI of less than 1 indicates the two antimicrobials interact in a synergistic manner.

While there are various methods known to individuals skilled in the art for measuring levels of antimicrobial activity, in the following examples the endpoint used is known as the Minimal Inhibitory Concentration, or MIC. This is the lowest concentration of a substance or substances which can achieve complete inhibition of growth.

In order to determine the Minimal Inhibitory Concentration, a two-fold dilution series of the antimicrobial is constructed with the dilutions being made in growth media. The dilutions are made in a 96 well microplate such that each well has a final volume of 280 µl of media and antimicrobial. The first well has, for example, a concentration of 1000 µM antimicrobial, the second 500 µM, the third 250 µM, and so forth, with the 12$^{th}$ and final well in the row having no antimicrobial at all and serving as a positive growth control. After the dilution series is constructed the wells receive an inoculum of microbe suspended in growth media such that the final concentration of microbes in the well is ~5×10$^5$ cfu/ml. In these examples the test microbe used is *Lactobacillus plantarum*. The cultures are incubated at 37° C. for 18-24 hours, and the wells scored as positive or negative for growth based on a visual examination for turbid wells, with turbidity being an indicator of growth. The lowest concentration of antimicrobial which completely inhibits growth (eg., a clear well) is designated the Minimal Inhibitory Concentration.

In order to determine whether the interaction between two antimicrobials is additive, antagonistic, or synergistic against a target microbe a modification of the MIC method known as the "checkerboard" method is employed using 96 well microplates. To construct a checkerboard plate the first antimicrobial is deployed using the two-fold serial dilution method used to construct an MIC plate, except that each of the eight rows is an identical dilution series which terminates after the eighth column. The second antimicrobial is deployed by adding identical volumes of a twofold dilution series at right angles to the first series. The result is each well of the 8×8 well square has a different combination of antimicrobial concentrations, yielding 64 different combinations in total. The 9$^{th}$ and 10$^{th}$ columns receive no antimicrobial at all and serve as positive and negative growth controls, respectively. After the checkerboard microplate is constructed, it was inoculated with *Lactobacillus plantarum*, incubated at 37° C., and scored as described for the MIC method.

Example 1

Synergy of Citric Acid with Sodium Propionate

Minimal inhibitory concentrations were determined for both citric acid and sodium propionate at pH 6 using the protocol described above with *Lactobacillus plantarum* as the test microbe. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and sodium propionate is greater than the effect of either antimicrobial alone. The amount of citric acid needed to inhibit bacterial growth is reduced by more than an order of magnitude, from 100,000 ppm to 3,125-6,250 ppm. The concentration of sodium propionate drops by at least 50 percent, from 100,000 ppm to a range of 12,500-50,000 ppm.

TABLE 1

| Used alone | | Used in Combination | | | |
|---|---|---|---|---|---|
| Citric Acid MIC (QA) ppm | Propionic Acid MIC (QB) ppm | Citric Acid MIC (Qa) ppm | Propionic Acid MIC (Qb) ppm | Citric Acid:Sodium Propionate Ratio | Synergy Index |
| 100000 | 100000 | 6250 | 12500 | 1:2 | 0.19 |
| 100000 | 100000 | 3125 | 50000 | 1:16 | 0.53 |

Example 2

Synergy of Citric Acid with Sodium Propionate

Minimal inhibitory concentrations were determined for both citric acid and sodium propionate at pH 5 using the protocol described above with *Lactobacillus plantarum* as the test microbe. Different pHs were used for testing because these weak organic acids have various pKa values that influence their efficacy. At pH 5, the MIC of citric acid is reduced from 100,000 ppm (pH 6) to 25,000 ppm. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and sodium propionate is greater than the effect of either antimicrobial alone. The amount of citric acid needed to inhibit bacterial growth is reduced by 50% or more, from 25,000 ppm to 3,125-12,500 ppm. The concentration of sodium propionate drops 50% or more, from 100,000 ppm to a range of 391-50,000 ppm.

TABLE 2

| | Used alone | | Used in Combination | | | |
|---|---|---|---|---|---|---|
| | Citric Acid MIC (QA) ppm | Sodium Propionate MIC (QB) ppm | Citric Acid MIC (Qa) ppm | Sodium Propionate MIC (Qb) ppm | Citric Acid:Sodium Propionate Ratio | Synergy Index |
| 2a | 25000 | 100000 | 25000 | 391 | 64:1 | 1.00 |
| 2b | 25000 | 100000 | 12500 | 391 | 32:1 | 0.50 |
| 2c | 25000 | 100000 | 6250 | 25000 | 1:4 | 0.50 |
| 2d | 25000 | 100000 | 3125 | 50000 | 1:16 | 0.63 |

Example 3

Synergy of Citric Acid with Potassium Benzoate

Minimal inhibitory concentrations were determined for both citric acid and potassium benzoate at pH 6 using the protocol described above with *Lactobacillus plantarum* as the test microbe. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and potassium benzoate is greater than the effect of either antimicrobial alone. The amount of citric acid needed to inhibit bacterial growth is reduced from 100,000 ppm to 390-6,250 ppm. The concentration of potassium benzoate drops from 100,000 ppm to a range of 780-12,500 ppm.

TABLE 3

| | Used alone | | Used in Combination | | | |
|---|---|---|---|---|---|---|
| | Citric Acid MIC (QA) ppm | Potassium Benzoate MIC (QB) ppm | Citric Acid MIC (Qa) ppm | Potassium Benzoate MIC (Qb) ppm | Citric Acid: Sodium Propionate Ratio | Synergy Index |
| 3a | 100000 | 100000 | 6250 | 780 | 8:1 | 0.07 |
| 3b | 100000 | 100000 | 3125 | 3125 | 1:1 | 0.06 |
| 3c | 100000 | 100000 | 1563 | 6250 | 1:4 | 0.08 |
| 3d | 100000 | 100000 | 780 | 12500 | 1:16 | 0.13 |
| 3e | 100000 | 100000 | 390 | 12500 | 1:32 | 0.13 |

Example 4

Synergy of Citric Acid with Potassium Benzoate

Minimal inhibitory concentrations were determined for both citric acid and potassium benzoate at pH 5 using the protocol described above with *Lactobacillus plantarum* as the test microbe. Different pHs were used for testing because these weak organic acids have various pKa values that influence their efficacy. pKa of Benzoate is At pH 5, the MIC of citric acid is reduced from 100,000 ppm (pH 6) to 25,000 ppm. The MIC of potassium benzoate was reduced from 100,000 ppm to 3,125 ppm when the pH of the media was lowered to 5. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and potassium benzoate is greater than the effect of either antimicrobial alone. The amount of citric acid needed to inhibit bacterial growth is reduced from 25,000 ppm to 3,125-12,500 ppm. The concentration of potassium benzoate drops from 3,125 ppm to a range of 391-1,563 ppm.

TABLE 4

| Used alone | | Used in Combination | | | |
|---|---|---|---|---|---|
| Citric acid MIC (QA) ppm | Potassium benzoate MIC (QB) ppm | Citric acid MIC (Qa) ppm | Potassium benzoate MIC (Qb) ppm | Citric acid:Potassium benzoate Ratio | Synergy Index |
| 25000 | 3125 | 12500 | 391 | 32:1 | 0.63 |
| 25000 | 3125 | 6250 | 391 | 16:1 | 0.38 |
| 25000 | 3125 | 3125 | 1563 | 2:1 | 0.63 |
| 25000 | 3125 | 1563 | 6250 | 1:4 | 2.06 |
| 25000 | 3125 | 781 | 6250 | 1:8 | 2.03 |
| 25000 | 3125 | 391 | 6250 | 1:16 | 2.02 |

The invention claimed is:

1. A method of controlling undesirable microorganism concentration in an aqueous system employed in a fermentation process, the method comprising the steps of:
   (a) introducing a fermentable carbohydrate to an aqueous solution;
   (b) introducing at least one yeast to said aqueous solution;
   (c) introducing a first organic acid and a second organic acid into the aqueous system, wherein the aqueous system comprises undesirable microorganisms wherein at least one undesirable microorganism is selected from the group consisting of lactic acid producing bacteria and acetic acid producing bacteria; and
   wherein the first organic acid is selected from citric acid, benzoic acid, or their salts; and wherein
   the first organic acid and a second organic acid is added to at least one stage in the fermentation process selected from liquefaction, propagation, conditioning and fermentation.

2. The method of claim 1 wherein the first organic acid is citric acid.

3. The method of claim 1 wherein the first organic acid comprises citric acid or its salt, and wherein the at least one second organic acid is selected from the group consisting of propionic acid, benzoic acid, or their salts.

4. The method of claim 1 wherein the first organic acid has a dosage rate of at least 100 ppm in the aqueous system being treated.

5. The method of claim 1 wherein the first organic acid has a dosage rate of at least 100 ppm and up to about 12500 ppm in the aqueous system being treated.

6. The method of claim 1 wherein the at least one first organic acid comprises citric acid, the at least one second organic acid comprises propionic acid or its salt, in which the ratio of citric acid to propionic acid is from 64:1 to 1:16 and the amount of the first organic acid is the aqueous system to be treated is from 100 to 12500 ppm.

7. The method of claim 1 wherein the at least one first organic acid comprises citric acid, the at least one second organic acid comprises benzoic acid or its salt, wherein the ratio of citric acid to benzoic acid is from 8:1 to 1:32, and the amount of the first organic acid is the aqueous system to be treated is from 100 to 12500 ppm.

8. A method of controlling undesirable microorganism concentration in an aqueous fluid solution employed in a fermentation process, the method comprising the steps of:
   (a) introducing a fermentable carbohydrate to an aqueous solution;
   (b) introducing at least one desirable microorganism which is capable of fermenting carbohydrate to said aqueous solution;
   (c) introducing at least one first organic acid into said aqueous solution; and
   (d) introducing at least one second organic acid into said aqueous solution, wherein the aqueous system comprises undesirable microorganisms wherein at least one undesirable microorganism is selected from the group consisting of lactic acid producing bacteria and acetic acid producing bacteria; and
   wherein the first organic acid is selected from citric acid, benzoic acid, or their salts; and wherein
   the first organic acid and the second organic acid is added to at least one stage in the fermentation process selected from liquefaction, propagation, conditioning and fermentation.

9. The method of claim 8 wherein the first organic acid is selected from the group consisting of citric acid, benzoic acid, and their salts.

10. A method of controlling undesirable microbial growth in fermentation broths or industrial fermentation processes or systems, the method consisting of the step of adding to a fermentation broth or industrial fermentation processes or system (a) at least one first organic acid and
   (b) at least one second organic acid wherein the first organic acid is different from the second organic acid, wherein the aqueous system comprises undesirable microorganisms wherein at least one undesirable microorganism is selected from the group consisting of lactic acid producing bacteria and acetic acid producing bacteria; and wherein the first organic acid is selected from the group consisting of citric acid, benzoic acid and their salts; and wherein the first organic acid and a second organic acid is added to at least one stage in the fermentation process selected from liquefaction, propagation, conditioning and fermentation.

11. The method of claim 10 wherein the first organic acid is citric acid.

12. The method of claim 10 wherein the first organic acid comprises citric acid or its salt, and wherein the at least one second organic acid is selected from the group consisting of propionic acid, benzoic acid, or their salts.

13. The method of claim 10 wherein the first organic acid has a dosage rate of at least 100 ppm in the aqueous system being treated.

14. The method of claim 10 wherein the first organic acid has a dosage rate of at least 100 ppm and up to about 12500 ppm in the aqueous system being treated.

15. The method of claim 10 wherein the at least one first organic acid comprises citric acid, the at least one second organic acid comprises propionic acid or its salt, in which the ratio of citric acid to propionic acid is from 64:1 to 1:16 and the amount of the first organic acid is the aqueous system to be treated is from 100 to 12500 ppm.

16. A method of controlling undesirable microorganism concentration in an aqueous system employed in a fermentation process, the method comprising the steps of:

(a) introducing a fermentable carbohydrate to an aqueous solution;

(b) introducing at least one yeast to said solution;

(c) introducing a first organic acid and a second organic acid said into the aqueous system, wherein the aqueous system comprises undesirable microorganisms wherein at least one undesirable microorganism is selected from the group consisting of lactic acid producing bacteria and acetic acid producing bacteria; and wherein the first organic acid is selected from citric acid, benzoic acid, or their salts; and wherein the first organic acid is added to a location in the fermentation process selected from the slurry tank, cook vessels, the mash, the propagation tanks, the conditioning tanks, the starter tanks, heat exchangers, the fermentation tanks during the simultaneous saccharification and fermentation stage and the piping between any of these units.

17. The method of claim 16 wherein the first organic acid is citric acid.

18. The method of claim 16 wherein the first organic acid comprises citric acid or its salt, and wherein the at least one second organic acid is selected from the group consisting of propionic acid, benzoic acid, or their salts.

19. The method of claim 16 wherein the first organic acid has a dosage rate of at least 100 ppm and up to about 12500 ppm in the aqueous system being treated.

20. The method of claim 16 wherein the at least one first organic acid comprises citric acid, the at least one second organic acid comprises benzoic acid or its salt, wherein the ratio of citric acid to benzoic acid is from 8:1 to 1:32, and the amount of the first organic acid is the aqueous system to be treated is from 100 to 12500 ppm.

\* \* \* \* \*